US00PP16593P2

(12) United States Plant Patent
Bergman

(10) Patent No.: US PP16,593 P2
(45) Date of Patent: May 30, 2006

(54) ***AZALEA* PLANT NAME 'PEARLS'**

(50) Latin Name: *Rhododendron hybrida*
Varietal Denomination: Pearls

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 91 days.

(21) Appl. No.: 11/049,224

(22) Filed: Feb. 1, 2005

(51) Int. Cl.
*A01H 5/00* (2006.01)

(52) U.S. Cl. ..... Plt./238

(58) Field of Classification Search ..... Plt./238
See application file for complete search history.

*Primary Examiner*—Kent Bell
(74) *Attorney, Agent, or Firm*—C. A. Whealy

(57) ABSTRACT

A new and distinct cultivar of *Azalea* plant named 'Pearls', characterized by its dark green-colored leaves that do not abscise during the cooling and forcing periods; uniform and outwardly spreading plant habit; freely branching habit; uniform and freely flowering habit; rapid flowering response; plants begin flowering about 24 days after cooling treatment; large and ruffled white-colored flowers with greenish centers; double hose-in-hose flower form; excellent postproduction longevity with plants maintaining good flower substance for about five weeks in an interior environment; and very good resistance to *Cylindrocladium* in inoculated trials.

2 Drawing Sheets

Botanical designation: *Rhododendron hybrida.*
Cultivar denomination: 'Pearls'.

BACKGROUND OF THE INVENTION

The present Invention relates to a new and distinct cultivar of *Azalea*, botanically known as *Rhododendron hybrida,* an evergreen greenhouse-forcing type *Azalea*, and hereinafter referred to by the name 'Pearls'.

The new *Azalea* is a product of a planned breeding program conducted by the Inventor in Alva, Fla. The objective of the breeding program is to create new *Azalea* varieties having uniform plant habit, profuse and uniform flowering response, dark green foliage, good foliage retention during the cooling and forcing periods, resistance to *Cylindrocladium* and excellent postproduction longevity.

The new *Azalea* originated from a cross-pollination made by the Inventor in February, 1995, in Alva, Fla., of the *Azalea* cultivar Athena, disclosed in U.S. Plant Pat. No. 9,439, as the female, or seed, parent with the *Azalea* cultivar Solitaire, disclosed in U.S. Plant Pat. No. 3,171, as the male, or pollen, parent. The new *Azalea* was discovered and selected by the Inventor as a flowering plant within the progeny of the stated cross-pollination in a controlled environment in Alva, Fla. in October, 1997.

Asexual reproduction of the new *Azalea* by terminal cuttings taken in controlled environment in Alva, Fla. since February, 1998, has shown that the unique features of this new *Azalea* are stable and reproduced true to type in successive generations.

SUMMARY OF THE INVENTION

The new *Azalea* has not been observed under all possible environmental conditions. The phenotype may vary somewhat with variations in environment such as temperature, daylength and/or light intensity without, however, any variance in genotype.

The following traits have been repeatedly observed and are determined to be the unique characteristics of 'Pearls'. These characteristics in combination distinguish 'Pearls' as a new and distinct cultivar:

1. Dark green-colored leaves that do not abscise during the cooling and forcing periods.
2. Uniform and outwardly spreading plant habit.
3. Freely branching habit.
4. Uniform and freely flowering habit.
5. Rapid flowering response; plants begin flowering about 24 days after cooling treatment.
6. Large and ruffled white-colored flowers with greenish centers.
7. Double hose-in-hose flower form.
8. Excellent postproduction longevity with plants maintaining good flower substance for about five weeks in an interior environment.
9. Very good resistance to *Cylindrocladium* in inoculated trials.

In side-by-side comparisons conducted in Alva, Fla., plants of the new *Azalea* differed from plants of the female parent, the cultivar Athena, in the following characteristics:

1. Plants of the new *Azalea* were more vigorous than plants of the cultivar Athena.
2. Flowers of plants of the new *Azalea* were white in color whereas flowers of plants of the cultivar Athena were light coral pink in color.

In side-by-side comparisons conducted in Alva, Fla., plants of the new *Azalea* differed from plants of the male parent, the cultivar Solitaire, in the following characteristics:

3. Plants of the new *Azalea* were denser than plants of the cultivar Solitaire.
2. Flowers of plants of the new *Azalea* were white in color whereas flowers of plants of the cultivar Solitaire were pink in color.

Plants of the new *Azalea* can be compared to the plants of the cultivar Irish Lace, disclosed in U.S. Plant Pat. No. 11,187. However, in side-by-side comparisons conducted in Alva, Fla., plants of the new *Azalea* differed from plants of the cultivar Irish Lace in the following characteristics:

1. Plants of the new *Azalea* were more vigorous than plants of the cultivar Irish Lace.
2. Plant habit of plants of the new *Azalea* was more spreading than plant habit of plants of the cultivar Irish Lace.

BRIEF DESCRIPTION OF THE PHOTOGRAPHS

The accompanying colored photographs illustrate the overall appearance of the new *Azalea*. These photographs show the colors as true as it is reasonably possible to obtain in colored reproductions of this type. Colors in the photographs may differ slightly from the color values cited in the detailed botanical description, which accurately describe the colors of the new *Azalea*.

The photograph on the first sheet comprises a side perspective view of a typical flowering plant of 'Pearls'.

The photograph on the second sheet is a close-up view of typical flowers and leaves of 'Pearls'.

DETAILED BOTANICAL DESCRIPTION

The aforementioned photographs and following observations and measurements describe plants grown in Alva, Fla. with three plants per 15- cm containers, in a polypropylene-covered shade house under commercial production conditions. During the production of the plants, day temperatures ranged from 13 to 38° C. and night temperatures ranged from 0 to 26° C. Plants were pinched at planting, pinched a second time about 12 weeks later, and then pinched a third time about 12 weeks after the second pinch. After sufficient flower bud development, plants were cooled at 3 to 5° C. for about four weeks to break flower bud dormancy. Plants were subsequently forced into flower under commercial production conditions in a polyethylene-covered greenhouse. Plants used for the photographs and description were about one year old.

In the following description, color references are made to The Royal Horticultural Society Colour Chart, 1995 Edition, except where general terms of ordinary dictionary significance are used.

Botanical classification: *Rhododendron hybrida* 'Pearls'.

Commercial classification: Evergreen greenhouse-forcing type *Azalea*.

Parentage:

*Female or seed parent.*—*Rhododendron hybrida* cultivar Athena, disclosed in U.S. Plant Pat. No. 9,439.

*Male or pollen parent.*—*Rhododendron hybrida* cultivar Solitaire, disclosed in U.S. Plant Pat. No. 3,171.

Propagation:

*Type.*—By terminal vegetative cuttings.

*Time to initiate roots.*—Summer: About five weeks at temperatures of 24° C. Winter: About six weeks at temperatures of 24° C.

*Time to develop roots.*—Summer: About nine weeks at temperatures of 24° C. Winter: About eleven weeks at temperatures of 24° C.

*Root description.*—Fine, fibrous, and white in color.

*Rooting habit.*—Freely branching.

Plant description:

*Plant form and growth habit.*—Perennial, evergreen; uniform and outwardly spreading plant habit; broad inverted triangle; moderately vigorous growth habit. Densely foliated. Uniform and freely flowering habit with numerous double hose-in-hose flowers per plant.

*Branching habit.*—Freely branching; about four primary lateral branches develop after the initial pinch (removal of terminal apex); numerous secondary and tertiary branches develop after the sequential second and third pinches.

*Plant height, soil level to top of flowers.*—About 28 cm.

*Plant diameter, area of spread.*—About 44 cm.

*Lateral branch description.*—Length: About 18.5 cm. Diameter at base: About 5 mm. Internode length: About 1.8 cm. Strength: Very strong. Texture: Young: Pubescent, fine brown hairs. Mature: Woody; pubescent, fine brown hairs. Color: Young: Close to 144A. Mature: Close to 165A.

*Foliage description.*—Arrangement: Alternate, single. Foliage retention: Very good foliage retention on plants of the new *Azalea* that have been in a box for six weeks during the cooling treatment. Length: About 4.9 cm. Width: About 2.3 cm. Shape: Mostly elliptic. Apex: Cuspidate. Base: Cuneate. Margin: Entire. Venation pattern: Pinnate. Texture, upper surface: Leathery, tough, durable; pubescent. Texture, lower surface: Leathery, tough, durable; mostly smooth; midveins and margins, pubescent. Luster, upper surface: Glossy. Luster, lower surface: Somewhat glossy. Color: Developing and fully expanded foliage, upper surface: Darker green than 147A. Developing and fully expanded foliage, lower surface: Close to 147B. Venation, upper surface: Close to 147A to 147B. Venation, lower surface: Close to 147B to 147C. Petiole: Length: About 8 mm. Diameter: About 3 mm. Texture, upper and lower surfaces: Pubescent. Color, upper and lower surfaces: Close to 144A.

Flower description:

*Natural flowering season.*—Spring after sufficient cool period. If forced, plants typically flower about 24 days after a four-week cooling treatment; rapid flowering response. Flowers persistent.

*Flower arrangement.*—Flower arranged singly at terminals with usually about three flowers per apex; uniform and freely flowering habit. Flowers face upward to mostly outward. Flowers rotate to somewhat star-shaped.

*Flower appearance.*—Double hose-in-hose flower form with numerous petals and petaloids; white-colored flowers with greenish centers.

*Fragrance.*—None detected.

*Flower diameter.*—Large, about 8.75 cm.

*Flower depth.*—About 3.3 cm.

*Postproduction longevity.*—Excellent postproduction longevity; under interior conditions, plants maintain good flower substance for about five weeks.

*Flower bud (before showing color).*—Length: About 1.2 cm. Diameter: About 7.5 mm. Shape: Ovoid. Color: Close to 144A.

*Petals/petaloids.*—Arrangement: Double hose-in-hose flower form; about three whorls of about 15 imbricate petals and petaloids fused at the base. Length, largest petal: About 5.1 cm. Width, largest petal:

About 4.3 cm. Shape: Beyond fused base, spatulate with rounded apex. Margin: Entire. Texture, upper and lower surfaces: Smooth, satiny. Color: When opening and fully opened, upper surface: Close 155D; towards the base, 145C to 145D; with development, greenish coloration fades slightly. When opening and fully opened, lower surface: Close to 155D; towards the base, 145C to 145D; with development, greenish coloration fades slightly.

*Sepals.*—No sepals observed, all transformed into petaloids.

*Peduncles.*—Length: About 1.6 cm. Diameter: About 2.5 mm. Angle: Mostly upright. Strength: Flexible; strong, Texture: Very pubescent. Color: Close to 144B.

*Reproductive organs.*—Androecium: All stamens transformed into petaloids. Gynoecium: Quantity of pistils per flower: One. Pistil length: About 2.3 cm. Style length: About 1.8 cm. Style color: Close to 145D. Stigma shape: Deformed. Stigma diameter: Less than 1 mm. Stigma color: Close to 144A. Ovary color: Close to 144A; heavily whiskered.

*Seed/fruit.*—Seed and fruit development have not been observed.

Weather/temperature tolerance: Plants of the new *Azalea* have been observed to be very tolerant to rain and wind. Plants of the new *Azalea* have been observed to tolerate temperatures from 0 to 38° C.

Disease/pest resistance: In inoculated trials that were conducted in Alva, Fla. during the summers of 2001, 2002 and 2003, plants of the new *Azalea* have been observed to be very resistant to infection by *Cylindrocladium.* Plants have been not observed to be resistant to pests and other pathogens common to *Azaleas.*

It is claimed:

1. A new and distinct *Azalea* plant named 'Pearls', as illustrated and described.

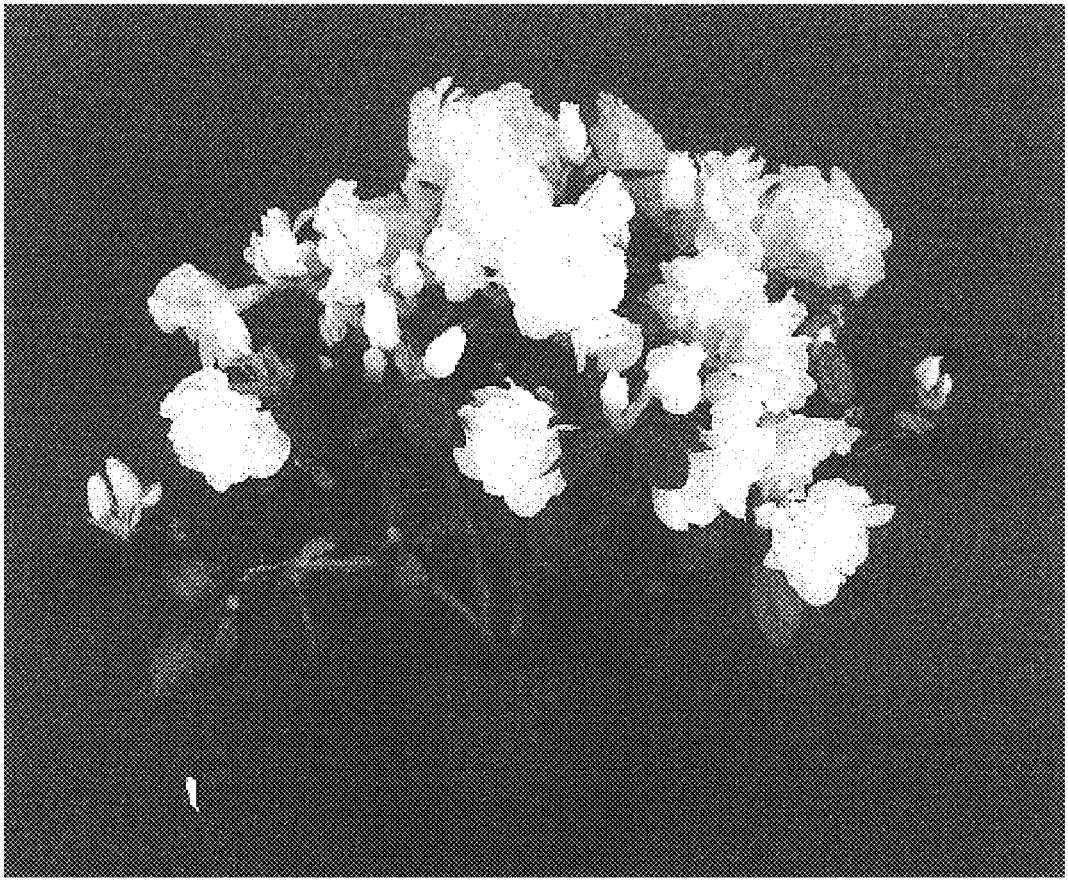

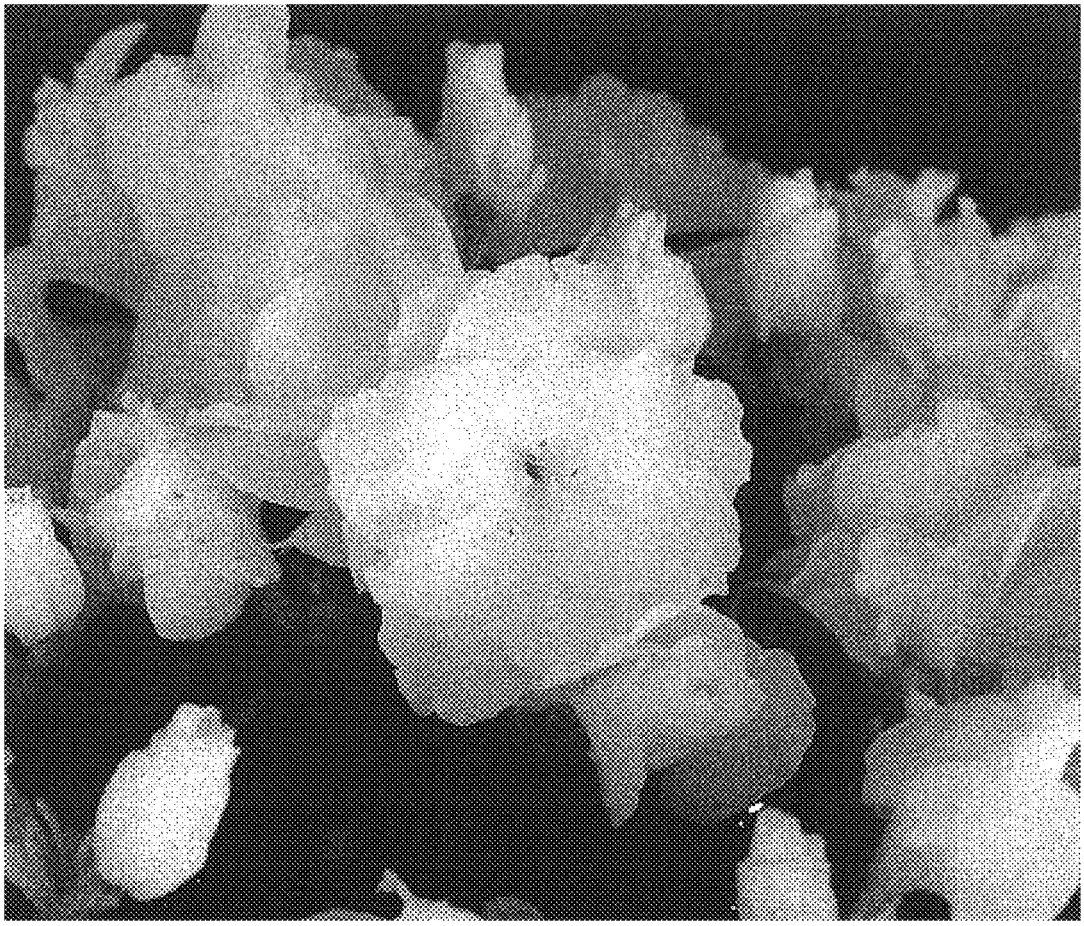

* * * * *